US007014999B2

(12) United States Patent
Finkelstein et al.

(10) Patent No.: US 7,014,999 B2
(45) Date of Patent: *Mar. 21, 2006

(54) TOPOGRAPHIC GENOTYPING

(75) Inventors: Sydney David Finkelstein, Aspinwall, PA (US); Patricia Anne Finkelstein, Aspinwall, PA (US)

(73) Assignee: RedPath Integrated Pathology, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/008,278

(22) Filed: Nov. 5, 2001

(65) Prior Publication Data

US 2002/0076724 A1 Jun. 20, 2002

Related U.S. Application Data

(63) Continuation of application No. 08/667,493, filed on Jun. 24, 1996, now Pat. No. 6,340,563, which is a continuation of application No. 08/311,553, filed on Sep. 23, 1994, now abandoned.

(51) Int. Cl.
  *C07H 21/04* (2006.01)
  *C12Q 1/68* (2006.01)
(52) U.S. Cl. .................. 435/6; 435/91.2; 536/23.1; 536/24.3; 536/24.33
(58) Field of Classification Search ................ 435/6.5, 435/91.2; 536/23.1, 24.3, 24.33
See application file for complete search history.

(56) References Cited

U.S. PATENT DOCUMENTS

| 5,320,840 A | * | 6/1994 | Camble et al. ............. 424/85.1 |
| 5,380,645 A | * | 1/1995 | Vogelstein ...................... 435/6 |
| 5,491,062 A | * | 2/1996 | McKenzie et al. .............. 435/6 |
| 5,580,728 A | * | 12/1996 | Perlin .............................. 435/6 |
| 5,843,644 A | * | 12/1998 | Liotta et al. .................... 435/6 |
| 6,340,563 B1 | * | 1/2002 | Finkelstein et al. ............ 435/6 |

OTHER PUBLICATIONS

Innis et al. PCR Protocols. Adademic Press, Inc. pp. 3-12, 153-158, 348-355, 1990.*
Teramoto et al. "Application of PCR to the microscopically identified cells on the slides" Acta Med. Okayama, vol. 48, No. 4, pp. 189-193, 1994.*
Shibata et al. "Specific Genetic Analysis of microscopic tissue after selective ultraviolet radiation fraction and the PCR", Am. J. of Pathology, vol. 121, No. 3, pp. 539-543, Sep. 1992.*
Kuppers et al. "tracing B cell development in human germinal centres by molecular analysis of single cells picked from histological sections", EMBO J. vol. 12, No. 13, pp. 4955-4967, 1993.*

Meltzer et al. Reduction to homozygosity involving p53 in esophageal cancers demonstrated by PCR. PNAS, vol. 88, pp. 4976-4980, Jun. 1991.*
Pretlow et al. "K-ras mutation in putative preneoplastic lesions in human colon". J. of Natl. Cancer Institute, vol. 85, No. 24, pp. 2004-2007, Dec. 1993.*
Erlich, Henry. PCR Technology. p. 8, 1990.*
Finkelstein SD, et al., "'Kras-2 topographic genotyping of pancreatic adenocarcinoma.',"  Arch. Surg., vol. 129 ( No. 4), p. 367-372, (Apr. 1, 1994).
Finkelstein SD, et al., "'Genotypic classification of colorectal adenocarconoma. Biologica behavior correlates with K-ras-2 mutation type.'," Cancer (1993), vol. 71 ( No. 12), p. 3827-3838, (Jun. 15, 1993).
Reincke M. et al., "'p53 mutations in human adrenocortical neoplasms: immunohistochemical and molecular studies.',"  J. Clin Endocrin. and Metabol. (1994), vol. 78 ( No. 3), p. 790-794, (Mar. 1, 1994).
Slebos, RJC, et al., "'K-ras oncogene activation as a prognostic marker in adenocarcinoma of the lung.',"  New Engl. J. Med. (1990), vol. 323 ( No. 9), p. 561-565, (Aug. 3, 1990).
Ben-Ezra et al., *"Effect of Fixation on the Amplification of Nucleic Acids from Paraffin-embedded Material by the polymerase Chain Reaction,"* The Journal of Histochemistry and Cytochemistry, 39(3), pp. 351-354 (1991) The Histochemical Society, Inc.
Talmadge, *"The pharmaceutics and delivery of therapeutic polypeptides and proteins,"* Advanced Drug Delivery Reviews, 10, pp. 247-299 (1993) Elsevier Science Publishers B.V., Amsterdam, Holland.

(Continued)

*Primary Examiner*—Jeanine A. Goldberg
(74) *Attorney, Agent, or Firm*—Drinker Biddle & Reath LLP

(57) ABSTRACT

The present invention pertains to a method for topographic genotyping. The method comprises the steps of placing a biological specimen having DNA of a patient under a microscope. Then there is the step of inspecting the biological specimen microscopically with the microscope. Next there is the step of choosing a microscope size target on the biological specimen based on its histopathologic characteristics. Next there is the step of separating the target from the specimen. Then there is the step of obtaining DNA sequences from the target so the DNA sequences can be amplified. Next there is the step of amplifying the DNA sequences. Then there is the step of detecting mutations in the DNA sequences. The present invention pertains to a method for topographic genotyping. The method comprises the steps of separating a section from a specimen of fixative treated tissue. Then there is the step of obtaining DNA sequences from the section. Next there is the step of amplifying the DNA sequences by cyphaling them in a PCR machine, with each cycle heating them to a temperature no greater than 99° C., and then back to a temperature of 55° C. in 5 minutes. Next there is the step of detecting mutations in the DNA sequences. Preferably, the separating step includes the step of cutting one to three 2–6 micron thick histeologic sections from the specimen.

29 Claims, No Drawings

OTHER PUBLICATIONS

Orkin et al., Report and Recommendations of the Panel to Assess the NIH Investment in Research on Gene Therapy (1995).

Gura "Antisense Has Growing Pains," Science, 270, pp. 575-577, (1995) Amer. Assn. For the Advancement of Science, Washington, D.C.

Stenersen et al., "The selection of thin epithelial layers: a method for single cell preparations of very small biopsies from the vocal cords," Analytical Cellular Pathology, 2, pp. 253-258, (1990) Elsevier Science Publishers B.V., Amsterdam, Holland.

Oud et al., "Extraction of Nuclei From Selected Regions in Paraffin-Embedded Tissue[1,2]," Cytometry, 7, pp. 595-600 (1986) Alan R. Liss, Inc., New York.

Sen et al., "Microdissected Double-Minute DNA Detects Variable Patterns of Chromosomal Localizations and Multiple Abundantly Expressed Transcripts In Normal and Leukemic Cells," Genomics, 19(3), pp. 542-551 (1994) Academic Press, Inc., San Diego, CA.

Cheung Wong, et al., "Mutations in BRCA1 from Fixed, Paraffin-Embedded Tissue Can Be Artifacts of Preservation," Cancer Genet. Cytogenet. 107, pp. 21-27 (1998).

A-M de Roda Husman et al., "Processing of long-stored archival cervical smears for human papillomavirus detection by the polymerase chain reaction," British Journal of Cancer (1995) 72, pp. 412-417.

S. Kösel et al., "Use of neuropathological tissue for molecular genetic studies: parameters affecting DNA extraction and polymerase chain reaction," Acta Neuropathol. (1994) 88, pp. 19-25.

Zhi-Ping Ren et al., "Recovering DNA and Optimizing PCR Conditions from Microdissected Formalin-Fixed and Paraffin-Embedded Materials," Pathobiology 2000; 68, pp. 215-217.

Carla De Giorgi et al., "Formalin-induced infidelity in PCR-amplified DNA fragments," Molecular and Cellular Probes (1994) 8, pp. 459-462.

Takayuki Murase, M.D., et al., "Influence of Histochemical and Immunohistochemical Stains on Polymerase Chain Reaction," The United States and Canadian Academy of Pathology, Inc., vol. 13, No. 2, pp. 147-151 (2000).

Florell M.D., "Preservation of RNA for Funcational Genomic Studies: a Multidisciplinary Tumor Bank Protocol," The United States and Canadian Academy of Pathology, Inc., vol. 14, No. 2, pp. 116-128 (2001).

Xavier de Lamballerie, et al., "Improved current methods for amplification of DNA from routinely processed liver tissue by PCR," Journal of Clinical Pathology 1994, 47, pp. 466-467.

S.F. An, et al., "Removal of inhibitor(s) of the polymerase chain reaction from formalin fixed, paraffin wax embedded tissues," Journal of Clinical Pathology 1991, 44 pp. 924-927.

P.J. Coates, et al., "Simplified procedures for applying the polymerase chain reaction to routinely fixed paraffin wax sections," Journal of Clinical Pathology 1991, 44, pp. 115-118.

Gillian Tully, et al., "Analysis of 6 VNTR loci by 'multiplex' PCR and automated fluorescent detection," Human Genetics (1993) 92, pp. 554-562.

Craig R. Miller, et al., "Assessing Allelic Dropout and Genotype Reliability Using Maximum Likelihood," Genetics 160, (Jan. 2002), pp. 357-366.

Jonine L. Bernstein et al., "Comparison of Techniques for the Successful Detection of BRCA1 Mutations in Fixed Paraffin-Embedded Tissue," Cancer Epidemiology, Biomarkers and Prevention, vol. 11, (Sep. 2002), pp. 809-811.

L.G. Dressler, et al., "Policy guidelines for the utilization of formalin-fixed, paraffin-embedded tissue sections: the UNC SPORE experience," Breast Cancer Research and Treatment 58, pp. 31-39 (1999).

M.P. Burton, et al., "Comparisoon of Histologic Stains for Use in PCR Analysis of Microdissected, Paraffin-Embedded Tissues," BioTechniques, vol. 24, No. 1, pp. 86-91 (1998).

Cecilia Williams, et al., "A High Frequency of Sequence Alterations is Due to Formalin Fixation of Archival Specimens," American Journal of Pathology, vol. 155, No. 5, (Nov. 1999), pp. 1467-1471.

John W. Gillespie, et al., "Evaluation of Non-Formalin Tissue Fixation for Molecular Profiling Studies," American Journal of Pathology, vol. 160, No. 2, (Feb. 2002), pp. 449-457.

Susan E. Goelz, et al., "Purification of DNA from Formaldehyde Fixed and Paraffin Embedded Human Tissue," Biochemical and Bio Physical Research Communications, vol. 130, No. 1, 1985, pp. 118-126.

Beverly Barton Rogers, et al., "Analysis of DNA in Fresh and Fixed Tissue by the Polymerase Chain Reaction," American Journal of Pathology, vol., 136, No. 3, Mar. 1990, pp. 541-548.

Kevin F. Forsthoefel, M.D., et al., "Optimization of DNA Extraction from Formalin-Fixed Tissue and Its Clinical Application in Duchenne Muscular Dystrophy," Anatomic Pathology, A.J.C.P, Jul. 1992, pp. 98-104.

James M. Rae, et al., "Genotyping for polymorphic druge metabolizing enzymes from paraffin-embedded and immunohistochemically stained tumor samples," Pharmacogenetics 2003, vol. 13, No. 8, pp. 501-507.

Jos C.F. M. Dressen, et al., "Allelic Dropout Caused by Allele-Specific Amplification Failure in Single-Cell PCR of the Cystic Fibrosis ΔF508 Delection," Journal of Assisted Reproduction and Genetics, vol. 13, No. 2, 1996, pp. 112-114.

P. Wiegand, et al., "DNA degradation in formalin fixed tissues," Pathologe, Nov. 1996; 17(6); 451-7 (abstract only).

* cited by examiner

TOPOGRAPHIC GENOTYPING

This application is a continuation of U.S. patent application Ser. No. 08/667,493, filed Jun. 24, 1996, now U.S. Pat. No. 6,340,563, issued on Jan. 22, 2002, which is a continuation of U.S. patent application Ser. No. 08/311,553, filed Sep. 23, 1994, now abandoned.

FIELD OF THE INVENTION

The present invention relates to the detection of diseases, including cancers or heredity based defects in patients. More specifically, the present invention relates to detecting diseases in patients from a biological specimen based on histopathologic characteristics of the specimens as observed on the microscopic level.

BACKGROUND OF THE INVENTION

Recent advances in genetic research, especially those focused upon cancer or inherited disorders, has led to the identification of new genes having specific patterns of DNA sequence alterations directly related to pathologic disease states (Weinberg R A, Oncogenes, Antioncogenes, and the Molecular Basis of Multistep Carcinogenesis. Cancer Res., 49:3713–3721, 1989). Central to this research is the Human Genome Project, a monumental world-wide scientific effort to fully map and sequence the human genome (Watson J D, The Human Genome Project: Past, Present, and Future. Science, 248:44–49, 1990). Together the results will provide a detailed blueprint of the normal Human genome together with a understanding of DNA damage upon which the diagnosis and treatment of many conditions may be formulated. Using this information, genetic based therapies have already been instituted, consisting of the introduction into selected cells of normal or modified human genes designed to integrate and function as part of the host genome (Anderson W F, Human Gene Therapy. Science, 256:808–813, 1992). These initiatives provide a strong stimulus for tissue based methods which can characterize in detail DNA sequence alterations in selected cellular components of normal and disease affected human tissues.

To realize the potential of the expanding database of DNA sequence information, it has become necessary to have available methods which can detect and characterize DNA sequence alterations in tissue specimens such as those routinely obtained during the medical management of patients. Presently, in clinical practice, genetic analysis usually requires a fresh and relatively large tissue sample secured independently of other specimens for diagnostic purposes. Realistically, many clinical specimens, for which genetic sequence information would be vitally needed, are of small size obtained through biopsy procedures. Moreover there exists a priority of tissue management in that proper histopathologic diagnosis is paramount demanding that adequate tissue first be secured and placed into appropriate fixative solutions to preserve morphologic integrity for accurate is histopathologic evaluation. Standard practices of genetic analysis are generally ineffective on specimens exposed to fixative agents (Ben Ezra J, Johnson D A, Rossi J, Cook N, Wu A, Effect of Fixation on the Amplification of Nucleic acids from Paraffin-Embedded Material by the Polymerase Chain Reaction. J. Histochem. Cytochem., 39:351–354, 1991). This has led some to the collection of fresh tissue in Freezer Banks, a process that is inconvenient, costly and very often not carried out in practice. In contrast stands the vast bulk of archival tissue specimens in the form of fixative treated, paraffin embedded tissue blocks. These tissue archives are present in all medical centers and contain valuable specimens from patients whose disease has been followed for many years as part of the normal clinical management. These informative specimens await a simple, effective means for their genetic analysis. Clinical practice is very much in need of easily applicable techniques for DNA sequence analysis from routinely prepared tissue blocks (Antonarakis S E, Diagnosis of Genetic Disorders at the DNA Level. N. Engl. J. Med., 320:153–163, 1989). The methods to be used should not be destructive to the blocks and must take advantage of the important insights gained through detailed histopathologic analysis. The techniques should be independent of archival storage time permitting the opportunity for long-term retrospective study. Finally the approach should be cost effective and timely to participate in everyday clinical decision making.

Topographic Genotyping (TG) is a novel system of tissue management comprehensive in scope specifically developed to address these specific issues enabling full DNA analysis within the context of traditional pathology. TG permits tissue specimens, routinely fixed in standard fixative chemical agents, of any size including minute needle biopsy specimens and cell blocks of cytology material, and of any age including those stored in paraffin for over thirty years, to be both fully available for standard histopathology examination as well as DNA sequence analysis. Furthermore, TG has been specifically designed to incorporate procedures for tissue and information handling allowing quick and easy clinical as well as research application. In essence TG is designed to allow the user to simply and effectively sample minute morphologic targets within fixative treated tissue specimens based on histopathologic and topographic considerations, which in turn may serve as the basis for detailed DNA sequence analysis. The results of TG is an integration of genetic and histopathologic features in a simple, reliable and cost effective manner for clinical application.

Solid tissue specimens, removed at surgery or through biopsy procedures, are exposed to fixative agents designed to prevent tissue breakdown and preserve morphologic integrity for microscopic analysis and archival storage. Fixatives, the most common being a 4% buffered solution of formaldehyde, cause their tissue preserving effect by a process of chemical crosslinking of cellular constituents including proteins, sugars and nucleic acids. Much of the tissue stabilizing effect of tissue fixatives is chemically irreversible (Greer C E, Oeterson S L, Kiviat N B, Manos M M, PCR Amplification from Paraffin-Embedded Tissues. Effect of Fixative and Fixation Time. Am. J. Clin. Path., 95:117–124, 1991). This tissue stabilizing and preserving chemical interaction, essential for microscopic analysis, greatly interferes with the manipulation of DNA for genetic investigation representing a major deterrent for general application of molecular analysis on fixed tissue specimens.

In order to meet the need for up to date genetic analysis, current medical practice recommends obtaining separate tissue specimens, not subject to chemical fixation, exclusively for the purpose of genetic analysis. When this involves a fluid specimen of homogeneous character such as a blood sample or bone marrow aspirate, division of the specimen for separate microscopic and molecular biologic analysis is usually accomplished fairly easily without involving interfering with traditional pathologic diagnosis. For many needle biopsy procedures, however, and in a variety of other circumstances of limiting tissue availability, a solid tissue sample will not be able to be appropriately divided and thus molecular examination would not be performed. Even in the case of large specimens, which might appear at first to provide generous amounts of tissue sample for genetic study, appropriate subdivision may not be feasible in as much as cellular heterogeneity cannot be fully appreciated until full tissue fixation and histopathologic examination is first performed. To derive the greatest benefit from genetic analysis, it is highly desirable to focus molecular analysis on selected tissue targets reflecting the cellular basis of disease processes. This in turn can only be achieved following thorough histopathologic examination. This is the essential condition that must be met if true and effective integration of pathology and molecular biology is to be achieved.

These realities provide a strong impetus to define new ways in which fixative treated tissue specimens should be handled to allow DNA structure analysis. Current protocols in this regard, while they may be available, are, in general, highly inefficient, difficult to apply widely in clinical practice and do not take histological considerations fully into account (Shibata D K, Arnheim N, Martin W J, Detection of Human Papilloma Virus in Paraffin-Embedded Tissue Using the Polymerase Chain Reaction. J. Exp. Med., 167:225–230, 1988; Wright D K, Manos M M, Sample Preparation from Paraffin-Embedded Tissues. in PCR Protocols: A Guide to Methods and Applications. Innes M A, Gelfand D H, Sninsky J J, White T J (eds). pp. 153–158, 1990, Academic Press, Berkeley, Calif.; Greer C E, Lund J K, Manos M M, PCR Amplification from Paraffin-Embedded Tissues: Recommendations on the Fixatives for Long-Term Storage and Prospective Studies. PCR Meth. & Applic. 1:46–50, 1991). There exists at present no systematic means to integrated morphologic and genetic analysis of solid tissue specimens. Authoritative sources have recommended a system of DNA extraction and precipitation analogous to that used with fresh tissue (Shibata D K, Arnheim N, Martin W J, Detection of Human Papilloma Virus in Paraffin-Embedded Tissue Using the Polymerase Chain Reaction. J. Exp. Med., 167: 225–230, 1988). Nucleic acid precipitation from fixative treated specimens is very inefficient with resultant low recovery yields for subsequent genetic analysis (Ben Ezra J, Johnson D A, Rossi J, Cook N, Wu A, Effect of Fixation on the Amplification of Nucleic acids from Paraffin-Embedded Material by the Polymerase Chain Reaction. J. Histochem. Cytochem., 39:351–354, 1991). This in turn demands sacrifice of large amounts of starting material which is impractical and highly undesirable in many instances. Genetic analysis of fixative treated tissues often require gross dissection of the paraffin block in the dry state, a procedure that is both uncontrolled, wasteful and destructive to the archival stored tissue. This approach fails to take into account important microscopic features since handling of the tissue in the paraffin block with the naked eye is not subject to fine microscopic control. Protocols direct one to scrape tissue off the slide with a scalpel. occasionally protocols suggest selecting the area according to structures seen using the human eye (not microscope) similarly ignore the benefits derived from careful histopathologic/topographic selection (Greer C E, Lund J K, Manos M M, PCR Amplification from Paraffin-Embedded Tissues: Recommendations on the Fixatives for Long-Term Storage and Prospective Studies. PCR Meth. & Applic. 1:46–50, 1991). Tissue sampling must be performed at the microscopic level responding to the unique topographic and histopathologic features that are present in an individual tissue specimen.

DNA extracted from fixative treated tissues is generally regarded as a relatively poor starting material for nucleic acid amplification, mutational analysis and DNA sequencing (Ben Ezra J, Johnson D A, Rossi J, Cook N, Wu A, Effect of Fixation on the Amplification of Nucleic acids from Paraffin-Embedded Material by the Polymerase Chain Reaction. J. Histochem. Cytochem., 39:351–354, 1991). Users are cautioned to this effect and advised to expect poor results. Yet in selected circumstances, these very same specimens may be shown to yield important genetic information indicating that given the right approach such tissue may be very informative. Despite the knowledge that specific DNA sequence alterations are frequently found involving oncogene and tumor suppressor genes commonly present in many forms of human cancer, there exists at present no effective means to broadly analyze fixative treated specimens of any size and age for clinical application of genetic information.

Topographic genotyping was developed to meet the needs for selection of fixed tissue for genetic analysis. The specific criteria upon which topographic genotyping is based are outlined in Table 1. TG is the only system at present which fully meets these necessary criteria for clinical application. TG furthermore includes the necessary organization of methodological steps and information flow for suitable clinical application at this time. While reports by others document the use of fixative treated tissues for genetic analysis none is uniquely designed to be fully integrated into traditional histopathology in a simple, reliable, efficient and cost effective fashion. Criteria for the topographic component as outline in Table 1 provide the essential link to merge modern genetic analysis into traditional pathology practice.

TABLE 1

TOPOGRAPHIC GENOTYPING: TOPOGRAPHIC COMPONENT CRITERIA FOR SUCCESSFUL APPLICATION

| BASIC CRITERIA | EXPANDED CRITERIA |
| --- | --- |
| EFFECTIVE ON FORMALIN-FIXED, PARAFFIN-EMBEDDED TISSUES WITHOUT UNDUE SPECIMENS SACRIFICE | EFFECTIVE WITH DIFFERENT TYPES OF FIXATIVES ARCHIVAL TISSUE BLOCKS OF VARYING STORAGE AGE |
| HISTOPATHOLOGIC & TOPOGRAPHIC SAMPLING GUIDED BY MICROSCOPIC CONSIDERATIONS | DETAILED SEPARATION OF MIXTURES OF CELLULAR COMPONENTS |
| CONFINED TARGETING INVOLVING MINUTE BUT HIGHLY REPRESENTATIVE TISSUE SAMPLING | SAMPLING OF NECROTIC, CRUSHED OR OTHERWISE UNSUITABLE SITES BIOPSY SIZED SPECIMEN HANDLING |
| CAPACITY FOR MULTIPLEX GENETIC ASSAYS WITHOUT THE NEED TO RECUT OR FURTHER SACRIFICE TISSUE | |

TABLE 1-continued

TOPOGRAPHIC GENOTYPING: TOPOGRAPHIC COMPONENT
CRITERIA FOR SUCCESSFUL APPLICATION

| BASIC CRITERIA | EXPANDED CRITERIA |
|---|---|
| CLINICAL APPLICATION CONSIDERATIONS | METHODOLOGICAL SIMPLICITY<br>EXPEDITED ANALYSIS FOR TIMELY RESULTS<br>HIGH EFFICACY WITH MINIMAL FAILURE RATE<br><br>COMPATIBILITY WITH EXISTING LABORATORY PRACTICES<br>COST EFFECTIVENESS OF TESTING<br>QUALITY ASSURANCE AND CONTROL |

SUMMARY OF THE INVENTION

The present invention pertains to a method for topographic genotyping. The method comprises the steps of placing a biological specimen having DNA of a patient under a microscope. Then there is the step of inspecting the biological specimen microscopically with the microscope. Next there is the step of choosing a microscope size target on the biological specimen based on its histopathologic characteristics. Next there is the step of separating the target from the specimen. Then there is the step of obtaining DNA sequences from the target so the DNA sequences can be amplified. Next there is the step of amplifying the DNA sequences. Then there is the step of detecting mutations in the DNA sequences.

The present invention pertains to a method for topographic genotyping. The method comprises the steps of separating a section from a specimen of fixative treated tissue. Then there is the step of obtaining DNA sequences from the section. Next there is the step of amplifying the DNA sequences by cyphaling them in a PCR machine, with each cycle heating them to a temperature no greater than 99° C., and then back to a temperature of 55° C. in 5 minutes. Next there is the step of detecting mutations in the DNA sequences. Preferably, the separating step includes the step of cutting one to three 2–6 micron thick histeologic sections from the specimen.

DESCRIPTION OF THE PREFERRED EMBODIMENT

The present invention pertains to a method for topographic genotyping. The method comprises the steps of placing a biological specimen having DNA of a patient under a microscope. Preferably, the biological specimen includes tissue sections, cytological fluids, filter or cellular specimens.

Then there is the step of inspecting the biological specimen microscopically with the microscope. Next there is the step of choosing a microscope size target on the biological specimen based on its histopathologic characteristics. Next there is the step of separating the target from the specimen. Preferably, the specimen is a tissue section and the separating step includes the steps of slicing the target from the section and placing the target on a glass slide. Alternatively, the specimen is a tissue section and the separating step includes the step of placing the target in a tube. Alternatively, the specimen is a filter and the separating step includes the steps of cutting an arc segment from a filter and placing the segment in a tube.

Then there is the step of obtaining DNA sequences from the target so the DNA sequences can be amplified. Preferably, the obtaining step includes the step of extracting the DNA from the target. Preferably, the extracting step includes the step of placing the target in a lysis buffer. Preferably after the step of placing the target in a lysis buffer, there is the step of adding phenol chloroform into the lysis buffer with the target. Preferably after the adding step, there is the step of separating short length fragments of DNA being less than 100 base pairs in length from the target.

Next there is the step of amplifying the DNA sequences. Preferably, the amplifying step includes the step of choosing a primer corresponding to a gene of the patient. Then there is the step of adding the primer to the DNA sequences. Next there is the step of forming polymerase chain reaction on the DNA sequences with the primer.

Then there is the step of detecting mutations in the DNA sequences. Preferably, the detecting step includes the step of determining the DNA sequence. Preferably after the determining step, there is the step of comparing the DNA sequence with known DNA sequences corresponding to DNA regions of the target. Preferably, after the detecting step, there is the step of establishing whether the DNA sequences are associated with the cancer, and applying a treatment regime to attack the cancer. Preferably, before the applying step, there is the step of identifying a source in the patient for the cancer. Alternatively, after the detecting, there is preferably the step of establishing whether the DNA sequence is associated with a condition hazardous to the health of a patient.

The present invention pertains to a method for topographic genotyping. The method comprises the steps of separating a section from a specimen of fixative treated tissue. Then there is the step of obtaining DNA sequences from the section. Next there is the step of amplifying the DNA sequences by cycling them in a PCR machine, with each cycle heating them to a temperature no greater than 99° C., and then back to a temperature of 55° C. in 5 minutes. Next there is the step of detecting mutations in the DNA sequences. Preferably, the separating step includes the step of cutting one to three 2–6 micron thick histeologic sections from the specimen.

For instance, once the DNA sequences have been amplified, either the step of detecting mutations in DNA sequences can be performed, or the step of identifying the DNA sequence can be performed. In essense, the step of detecting the mutations can either be through identifying the nucleotides in the DNA sequence or through a comparative technique where the individual nucleotides of DNA sequence do not necessarily need to be identified, but simply by having a comparison which matches with a known DNA sequence which conforms to a predefined cancer, the DNA sequence can be used to identify that the specific cancer also exists in the patient. This, of course, is applicable for not just cancer but defective genes resulting from heredity or for diseases. If it is desired to specifically identify nucleotides of the DNA sequence, then the identifications specifically can be used again to compare known DNA sequences that are associated with given cancers or diseases or genetic abnormalities to heredity. These known DNA sequences can be obtained from established libraries that maintain such information and can be searched similar to, for instance, the way fingerprints are searched, although in this case, one would not need to have a graphic match, but instead would just compare the nucleotide sequences themselves for match. Once the given abnormality associated with a specific type of cancer or disease or hereditarial defect is identified, much information can be obtained, for instance, with cancers, since they have a unique DNA sequence associated with a specific type of cancer, If a breast cancer is determined in a patient, and several years later, a nodule is detected in another part of the body, then a biopsy will be taken of the nodule. The nodule will be analyzed as explained below, and its DNA sequence will be reviewed. Upon revealing or identifying its DNA sequence, it can be determined whether the source of the DNA was a cancer associated with the breast. Then the course of treatment for the nodule could be better identified since the origin of the cancer is known and it is appropriate to apply a therapy that can attack a breast cancer based origin.

Similarly, by identifying the DNA sequence and comparing it to known cancers, not only can the cancer be determined, but the stage of the cancer can be determined. If the cancer is in an early stage, then it might be indicative of chemotherapy or radiation treatment of a certain dosage or a certain chemical. If the cancer is in a later stage, it might be more indicative of a more aggressive type of therapy which might have greater side effects but might be necessary in order to save the life of the patient. Since it is recognized that cancers do not occur essentially in periods of days or weeks but take time for the DNA sequence to mutate and the cancer to arise, it is important to identify the DNA sequence to more accurately create a therapy regime which can attack and eradicate the cancer. The more information is known about the cancer or the disease, the better the therapy regime can be developed.

Topographic Genotyping (TG) refers to a multistep process complementing traditional histopathology that utilizes novel adaptations allowing fixative treated specimens to be subject to detailed DNA sequence analysis (Table 2). TG extends traditional analysis by enabling the genetic analysis to be conducted on microscopic sized targets selected from tissue sections based on histopathologic characteristics. Analysis can be applied to all sized specimens including archival samples. With minimal modifications, other types of clinical samples such as cytological fluids, filter and cellular specimens can be similarly analyzed. TG integrates histopathologic and genetic information in a format that is designed to be sensitive, specific, timely and cost effective while at the same time not being destructive of archival tissue or competitive with established medical practices. TG is organized so that the user is constantly in touch with the progress of each test specimen which can be reported and evaluated for aspects of quality assurance and control. Topographic genotyping is specifically designed to enable the microscopist to select, at leisure and in the comfort of his/her workbench, one or more microscopic sites within a tissue specimen for detailed DNA sequence analysis.

The general outline of TG is shown in Table 2. Tissues undergo traditional fixative treatment as currently performed in hospital and laboratories worldwide. Microscopic sections are prepared and stained for proper morphologic evaluation and histopathologic diagnosis. There is no interference or delay in well established pathology practices. Moreover specific aspect of histologic handling of tissues, known to vary from one institution to another such as the duration and temperature of various individual steps, exerts no detrimental effect. TG is fully compatible with routine practice variations.

One or more topographic targets are selected based on histopathologic considerations. These targets are minute in size and highly representative of the cellular alterations to which they are related. Tissue blocks are recut, baked and deparaffinized (as routinely done prior to histological staining) to allow topographic sampling directly from unstained blank sections. Minute but highly representative target samples are collected in a 0.5 mL microtube referred to as a storage unit from which up to 30 different DNA sequence analyses can be performed immediately or at any later time. This storage unit represents the link between histopathology and DNA sequence analysis enabling DNA sequence alterations to be intimately related to cellular alterations of specific disease processes. At no time are tissue blocks damaged or excessively utilized thus tissue remains available for future histological or genetic examinations.

An aliquot of the storage unit is subject to DNA amplification followed by direct sequencing to elucidate specific DNA sequence alterations. TG incorporates unique modifications optimizing DNA amplification of fixative treated DNA. Efficient and specific nucleic acid amplification is the most critical step when processing fixative treated DNA. TG has been formulated upon a scientific basis which best explains and addresses the implications of fixative treatment for DNA amplification. Greater than 95% efficiency is achieved even for old archival fixative treated, paraffin embedded tissue blocks. DNA amplification is followed by DNA sequencing permitting comparative sequence analysis of samples within and between cellular areas within tissue specimens. Alternatively other general screening or detailed mutational analysis method may be used to search for DNA structural damage. In this way genetic information is integrated with pathologic findings. The timetable to accomplish this analysis is included in Table 2. Using the day of initial specimen receipt as 'day 1', histopathologic evaluation is generally completed on days 2–3. TG is designed to provide genetic information for integrated analysis by day 5 meeting the timely needs of clinical practice to have genetic information readily available at the earliest moment. Since TG is equally effective on biopsy specimen, genetic information can be provided based on biopsy specimens to assist planning of most involved surgical or medical procedures.

TG includes several unique aspects of special value in the clinical management of patients suspected of genetic related disease states. Tissue sampling is generally carried out only once without the need to repeatedly section the tissue block thereby avoiding unnecessary sacrifice of tissue. The topographic tissue samples can be stored indefinitely and returned to at future dates for additional genetic analyses. Appropriate elements of quality assurance and control are included for clinical laboratory institution as well as informatics organization design. TG can easily be scaled up to handle large numbers of tissue samples. TG consists of simple laboratory methods and instrumentation encouraging broad and easy application. In these ways TG represents a novel and important advance providing modern medicine with an effective tool for the handling of tissue specimens leading to better diagnosis and treatment.

for detailed gross dissection which can not be effectively performed when hastily carried out on fresh unfixed tissues. Avoidance in the handling of fresh tissue is most attractive in the examination of potentially infectious tissue specimens is it lessens the risk of exposure to blood borne infections such as AIDS.

TABLE 2

TOPOGRAPHIC GENOTYPING: GENERAL OUTLINE

| BASIC PROCEDURE | ANCILLARY PROCEDURES | TIME-TABLE |
| --- | --- | --- |
| TISSUE FIXATION | PRELIMINARY SAMPLING | DAY 1 |
| GROSS DISSECTION | | |
| HISTOLOGIC PREPARATION | DIRECT MINUTE TARGET SAMPLING | DAY 2 |
| MICROSCOPIC EVALUATION | HISTOPATHOLOGIC DIAGNOSIS TOPOGRAPHIC SITE SELECTION | DAY 2 |
| TOPOGRAPHIC SAMPLING WITH CREATION OF THE TOPOGRAPHIC STORAGE UNIT | GENE SELECTION | DAY 2 |
| NUCLEIC ACID AMPLIFICATION | OLIGONUCLEOTIDE PRIMER DESIGN FOR DNA AMPLIFICATION AND SEQUENCING | DAY 3 |
| DNA SEQUENCING WITH MUTATION DETECTION | GENETIC DIAGNOSIS LEADING TO INTEGRATED GENETIC/ HISTOPATHOLOGIC DIAGNOSIS | DAY 4–5 |

Specific Description of Components of Topographic Genotyping Specimen Selection:

Virtually any fixative-treated, paraffin-embedded tissue specimen can be effectively subject to DNA sequence analysis using TG. Standard fixative agents such as formaldehyde, BouinÔs, B5, and some mercury containing solutions do not interfere with topographic genotyping. Exceptions include strong acid decalcifying solutions which cause extensive DNA damage. Undecalcified bone section may be utilized. Conditions of fixation such as duration of time between initial fixation and variations in tissue processing are not a critical factor. The user of TG is free to investigate archival fixed tissues for detailed DNA sequence alterations.

In TG, the user selects one or more microscopic sized targets irrespective of shape or size in the tissue section of interest. For example cellular alterations in very confined areas such as might be detected following the use of special procedures such as immunohistochemical staining may serve as the basis for topographic sample selection. Small, needle biopsy specimens or cytological cell blocks prove quite satisfactory. Archival age is not a detrimental factor with specimens thirty years and older being capable of analysis. Complex mixtures of tissue types including disease related and normal elements can be dissected and evaluated separately. In addition segments of cytological filter preparations or portions of cell pellets with or without fixation can be analyzed. Hence the user of TG would have the opportunity to carry out virtually any type of retrospective analysis on specimens of his/her choice.

The microscopist would most often utilize TG when examining tissue specimens harboring or suspected to be containing microscopic evidence of cancer. In the case of large complex specimens such as surgical resections, TG would free the user from the need to obtain fresh tissue for frozen storage. Rather, the user would have the assurance that detailed DNA analysis could follow full tissue fixation. The latter is essential as a means to properly set the tissue up In the course of gross dissection, one or more targets can be selected based on macroscopic appearance of the carefully dissected specimen. These macroscopic selected specimens are taken in a preliminary fashion as full topographic and histopathologic significance would be confirmed by microscopic analysis. Supplemental topographic sampling may be required based on precise microscopic features. These preliminary samples could begin the genotyping analysis with results available on the fourth day by commencing the genetic component one day earlier (Table 2). This variation on the use of TG to analyze selected tissue specimens from the gross fixed specimen has broad application by encouraging consideration and incorporation of genetic evaluation into traditional pathology practice. At the end of a typical working day, the gross dissector may conveniently accumulate a series of individual samples that can then be processed in a batch for specific DNA sequence alterations without significant time delay to standard gross fixed tissue dissection and analysis. The representativeness of the sample obtained at gross dissection would be subsequently judged at the time of microscopic evaluation at which point additional topographic targets may be chosen as required.

At the time of microscopic evaluation, the microscopist can simply place one or more ink dot marks on each site he/she wishes to analyze for DNA sequence alterations. The tissue blocks are retrieved and 1–4 four micron thick sections are cut as is general routine for typical recuts. In the case of minute discrete targets such as biopsy specimens, sampling takes place directly from the waterbath as described below. The sampled tissue is collected in 0.5 mL microtubes referred to as storage units which may be returned to for repeated genetic analyses without the need to recut the tissue block. The approach for target selection is again shown to be very broad enabling virtually any tissue specimen of any size to be subject to integrated genetic/histopathologic analysis.

Gene Selection and Oligonucleotide Primer Design:

With TG, any region of a gene can be amplified provided sufficient sequence information is available upon which to formulate amplifying and sequencing primers; short DNA sequences, 18–30 base pair long, most easily created by means of an oligonucleotide synthesizer apparatus. These primers direct the amplification and sequencing of DNA in TG. Oligonucleotide primer pairs are usually designed to amplify a genomic region approximately 200 base pairs in length, although longer lengths can be effectively amplified from fixative treated tissues. Either amplifying primer can serve as a sequencing primer, but design and use of an internal primer may in some case be worthwhile to achieve a clean sequencing band pattern. As sequencing will be performed by means of dideoxy chain termination with $^{35}S$ radionucleotide incorporation, it is important to select a radionucleotide that will be incorporated as close to the 3Õ end of the ultimate sequencing primer, ideally within three bases and several times within the first bases.

TG is valuable as it enables the operator to freely investigate any genetic target for DNA sequence alterations from any type of fixative treated specimen. The only requirement is a minimum of sequence information upon which to design oligonucleotide primers. This genetic information is usually found in scientific manuscripts as well as in general repositories of genetic sequence information such as GenBank and EMBL and other genetic database resources readily available through network communication services. A typical application of TG would involve a potential user selecting a series of archival tissue blocks and a gene of interest for which the sequence information would be obtained. Once oligonucleotide primers have been made, the user would search for DNA sequence alterations following the guidelines and recommendations included in TG.

Histology Preparation:

Once one or more targets are selected for topographic analysis, tissue blocks are routinely sectioned at 4 microns on a microtome and floated in a water bath. For most application 1 to 4 tissue sections are sufficient to create a storage unit for 20 to 30 genetic analyses. The sections are picked up on glass slides and baked for 3 hrs. in a 55° C. oven. No special precautions are required other than avoidance of contact with post amplification products. Several sections may be placed on a single glass slide. Even minor folding within the tissue section is acceptable provided the target can be adequately visualized. Less than perfect recuts that otherwise would be discarded can be source of material for topographic selection further minimizing expenditure of tissue. With a minimum of experience, the histology technician can quickly learn to anticipate the tissue needs for TG leading to highly efficient tissue usage.

When selected targets are small such as biopsy specimens, they may be taken directly from the waterbath into the storage vial without the need to scrape directly from glass slides. Direct sampling from the waterbath is completely novel resulting in a simple yet highly efficient means utilize tiny specimens. Direct sampling does result in the inclusion of paraffin in the storage unit. This, however, is not an interfering factor since high temperature treatment of the storage unit after collection of the specimen is sufficient to free the tissue of its paraffin wax surround.

With experience, the technologist responsible for direct topographic selection from the waterbath will be able to successfully sample a wide array of specimens with this approach. Tissue remaining after direct sampling can be picked up on glass slides if desired and stained to evaluate the accuracy of direct sampling ensuring a means to assess quality assurance in direct topographic sampling.

Protocol: Direct Topographic Selection from Floating Paraffin Sections

PRINCIPLE OF TEST: When a specific target is small and well localized, it can be dissected directly from the water bath using fine probes bypassing sampling from glass slides.

REAGENTS: Deionized $H_2O$, ice and Topographic Lysis Buffer (100 mM NaCl, 25 mM EDTA pH 8.6, 10 mM Tris pH 8.3, 0.5% $NP_{40}$).

INSTRUMENTATION: Microtome and blade, float water bath, paint brush, fine picks, tissue papers, and 0.5 mL tubes, 4° C. refrigerator and/or −20° C. freezer Microscopist reviews slides and marks area to be sampled. Matching paraffin block is cooled on ice in preparation for microtomy.

Heat deionized water in tissue float between 50–55° C. (above melting temperature of paraffin). Cut tissue on microtome and place ribbon of tissue in water bath. Raising the temperature partially melts the paraffin and allows the tissue to float free.

Use a fine probe to lightly touch area of interest and pluck from water. To aid in accurate selection, use a second probe to hold back unwanted tissue. Place in empty 0.5 mL tube and repeat until sample collected. Add 25 $\mu$l of Topographic Lysis Buffer 1 to tube (see below).

Residual tissue can be picked up on a glass slide and stained to confirm accuracy of sampling. This direct method is not suitable for large samples as the target tissue doesn't usually separate easily from the whole, unless well encapsulated or otherwise demarcated from surrounding unwanted tissue.

To avoid contamination between samples, clear water bath of previous samples by sweeping with tissue paper. Wipe probes clean.

Variation: Direct Sampling of Cytological Filter Speciments

Cytology fluid specimens, in the form of cytocentrifuged or vacuum suctioned filter preps can be handled in a direct fashion. One or more cytology filter arc segments, approximately 45 degrees in size, are cut and placed in empty storage tube to which lysis buffer is added. A similar approach is used when handling cytological brushes or similar materials containing cellular material. The storage unit is then processed as described below.

Topographic Sampling from Glass Slides:

Topographic sampling from glass slides based upon microscopic considerations is the foundation that links genetic analysis with histopathology. It is by this detailed selection process that cellular heterogeneity may serve as the basis for integrated genetic/pathologic analysis. The unique contribution of TG is the ease by which even minute tissue targets from cellular heterogeneous specimens can be processed for multiple gene sequence alterations. With practice, even complex admixtures of cellular specimens can readily be dissected into individual units for comparative genetic evaluation.

Topographic sampling from slides is effective for virtually all tissue sections irrespective of individual histology practices. Unstained slides may be prepared in another institution then sent to a central laboratory for the genetic analysis component. The technique is not harmed by storage of undeparaffinized sections which may be kept for long periods of time and then processed.

Topographic selection of tissue based on microscopic considerations is intended to optimize sample selection and purity. Cellular characteristics as well as histochemical and immunohistochemical features serves as the basis by which the configuration of target areas are planned. The minute but highly representative nature of the tissue sample allows detailed integration of morphologic and genetic findings enhancing the overall information derived from the specimen. Even small biopsy specimens can be carefully dissected into distinct regions for comparative genetic analysis. For example in the case of a biopsy of malignant melanoma of the skin, the overlying squamous epithelium can first be removed and analyzed for genetic changes that correspond to the stage of intraepithelial growth. The superficial and deep components of an invasive tumor can be discretely sampled and analyzed separately. In this way TG represents the only means to effectively analyze such samples for DNA sequence alterations in as much as the primary skin tumor is usually small and cannot be divided for storage in a frozen tumor. bank. TG would provide the means to conduct DNA sequence analysis on this specific type of tissue specimens which at present is greatly lacking. TG would ensure that abundant material would still remain in the paraffin block for future investigation.

Protocol: Topographic Dissection from Glass Slides

PRINCIPLE OF TEST: Slides, blocks and patient data/records are reviewed. The best specimen slide or slides is/are selected, the areas of interest marked and unstained tissue sections are prepared for topographic dissection under a dissecting microscope. Dissection based on histopathology allows complex mixtures of tissue to be dissected and analyzed separately. DNA damage can be related to cellular alterations. Even microscopic sized targets consisting of small collections of cells can be analyzed.

REAGENTS: Ice, Xylene, graded EtOH (100%, 95%, 70%), Topographic Lysis Buffer 1 (100 mM NaCl, 25 mM EDTA pH 8.6, 10 mM Tris pH 8.3, 0.5% $NP_{40}$), Sampling Buffer (2% $NP_{40}$ in $H_2O$). Both Topographic Lysis Buffer 1 and Sampling Buffer are stored either at room temperature or in 4° C. refrigerator.

INSTRUMENTATION: Chemical hood, timers, staining jars, slide racks, slide holders, dissecting microscope, fine scalpel blade, sterile plastic transfer pipette, 0.5 mL sterile tube, tube racks, permanent marker, pipettor and tips, tissue float bath, microtome and blades and incubator oven, pretreated glass slides. (Pretreat slides by dipping into solutions to help tissue adhere to slides. Poly-L-Lysine, silane solutions or other agents may be used to assist adherence of tissue sections (only egg albumen can not be used).

Microscopist reviews histology slides and marks one or more target areas. An appropriate number of unstained recuts are prepared based target size. When blocks have been cooled on ice, cut 4–8 microns on microtome and float in water bath. Pick up tissue on glass slides and label with block #. Bake 3–18 hr. in 50° C. oven to optimize adherence.

Slides are deparaffinized in Xylene (5 min.×2), 100% EtOH (5 min.×2), 95% EtOH (5 min.×2), 70% EtOH (5 min.×2). then air dried. (Limited hood space; Xylene (10 min.), then 100% EtOH (10 min.). Change reagents often).

Arrange slides in slide holder with matching stained slide. Tissues may be left in a clean environment for several days awaiting Topographic Selection. Steps 1–3 may be done in histology lab. To avoid contamination of samples, from this point onward all tubes, pipette tips, etc. are sterile and all solutions are made with autoclaved deionized water, unless noted.

Fill 0.5 mL tubes with 25 µL Topographic Lysis Buffer (100 mM NaCl, 25 mM EDTA pH 8.6, 10 mM Tris pH 8.3, 0.5% $NP_{40}$) and close. Buffer lyses cell and nuclear membranes to extract DNA.

Barely dampen target region with Sampling Buffer (a drop or bubbles), blot or air dry excess. Place slide on stage of dissecting microscope and examine under dark field optics. Use scalpel tip to scrape target site into a clump, lift off glass and place in Topographic Lysis Buffer in tube. Detergent action of sampling buffer releases tissue into buffer. Add sampling buffer as needed. Repeat until sufficient sample collected then close tube.

Highly detailed topographic dissection takes advantage of the ability of minimally wetted tissue to be cleanly separated from adjacent dry tissue. Insert clean scalpel tip into Sampling Buffer. The drop of Buffer adhering to tip is then precisely placed at point of sampling. Carry this region over to the next site to continue sampling.

Typically 0.25 to 0.50 $cm^2$ area of tissue is placed in Topographic Lysis Buffer filled tube. For Quality Assurance, post-sampling slides can be stained to assess accuracy of topographic selection.

Samples may be stored in a refrigerator 4° C. for up to a week, or −20° C. freezer for years prior to further processing.

Scientific Basis or Effective DNA Amplification from Minute Topographic Samples of Fixative Treated Tissue Specimens The rate limiting step when handling fixative treated tissue specimens for genetic analysis is effective and specific DNA amplification. Unlike pure DNA that is extracted from fresh or frozen tissues, DNA that has been exposed to chemical fixative such as formaldehyde are often unsuccessfully or only poorly amplified. While the reason for the inability to efficiently amplify fixed tissues is known to be related to chemical action of the fixative agent upon nucleic acids, the precise mechanism most directly related to poor amplification is only poorly understood. The most suitable measures to overcome this detrimental effect are therefore not fully appreciated. Instead, recourse is usually taken to sacrificing large amounts of fixative treated tissue or abandoning the use of fixative treated tissues altogether.

It is a misconception that fixative treated tissue provides an inadequate amount of starting DNA for nucleic acid amplification. In reality, the tissue obtained from one to three 4 micron thick histologic sections of a small biopsy specimens, when handled properly, provides sufficient material for consistent and effective DNA amplification. In fact, when one attempts to add more fixative treated tissue to the amplification reaction, the tendency is to abolish successful amplification. This result is likely due to a combination of factors. This would include absorption of the Taq polymerase enzyme on the large amount of fixative exposed DNA that is provided by a large tissue specimen. Also errant amplification is likely when overloading the reaction with tissue and is reflected in the generation of broad smear of low and high molecular weight DNA. It is vitally important to use a small rather than a large amount of tissue to initially trigger the amplification reaction. Once triggered in the first few cycles to copy a sufficient quantity of DNA from the tissue template, the remainder of the amplification reaction goes forth in the buffer solution without significant participation of the original tissue DNA.

It is also generally held that the effect of tissue fixation is to induce irreversible cross linking of DNA and associated histone proteins that will prevent proper denaturation of the DNA in response to elevation in temperature (4), incorporated by reference. This is supported by the need to commence amplification with a series of high temperature denaturation steps early in the amplification process. This effect however is minor as demonstrated by the negative effect of high temperature annealing steps which invariably abolish amplification. In fact annealing and polymerization steps should be conducted at relatively low temperatures than that used when amplifying pure DNA. It is for this reason that two step amplification programs and shortening of the time duration of cycling program plateau phases has precisely the opposite effect than that theoretically expected. By the same token introduction of denaturing agents such as glycerol or DMSO, are found to exert no effect or have a negative impact on amplification.

It can be shown that the most important effect of tissue fixation on DNA is a loss in processivity that results from chemical modification of DNA causing the enzyme polymerization to prematurely terminate or fall off the fixative treated DNA template resulting in the production of a shorter than desired amplicon fragment. This short fragment may in a subsequent annealing step attach to an inappropriate site triggering undesirable polymerization which will result in inclusion of primer annealing sites on both ends of the nonspecific fragment. In turn this will lead to discrete nonspecific amplification bands or more often a wide range of amplified DNA reflected as a broad smear on agarose electrophoresis. It is the usual practice to raise both annealing and polymerization temperature to antagonize mispriming as discussed above but given the ease with which polymerization is terminated, this raising of temperature will have precisely the opposite effect intended. The phenomenon of premature termination is a most important factor leading to inefficient amplification and therefore measures which directly address this factor will have the most beneficial effect in the situation of fixative treated DNA.

High temperature denaturation is most valuable in the first five amplification cycles to produce maximal DNA template relaxation in anticipation of primer annealing. For most tissue specimens and gene targets this precaution together with experimentation to identify optimal functioning primers proves sufficient to achieve effective amplification. When this is found still to be inadequate, treatment of the storage unit with phenol chloroform washing as described below without the need for precipitation will confer effective amplification. This positive effect of phenol chloroform washing is due to more vigorous removal of DNA binding proteins that remain despite treatment with proteinase K. These adherent proteins may contribute to loss of processivity.

In a small minority of cases phenol-chloroform washing will not be sufficient to allow effective specific DNA amplification. For these infrequent cases one may resort to filter separation of small molecular weight DNA to confer effective amplification. This step is designed to separate small molecular weight short fragments of DNA from the storage tissue unit which may engage in the amplification reaction or contribute to premature termination of polymerization in the early amplification cycles. Filter separation as described below is conveniently formatted so that a minimum of manipulation is required to prepare the storage unit for amplification.

Once DNA amplification has been carried out from a fixative treated tissue specimen it is vital that rigorous separation of primers and most importantly small sized nonspecific amplification products be performed in such a way as to isolate the desired amplification product as purely as possible. Due to the factors listed above, fixative treated tissues tend to produce a relatively greater amount of such nonspecific products which can be seen as a smear effect on horizontal gel electrophoresis. If these products are carried into the subsequent genotyping steps such as DNA sequencing, they may result in artificial bands or weak ineffective sequencing reactions. The best approach to isolating specific amplification product is to carry out agarose gel electrophoresis at relatively high agarose concentrations such as 3% to most effectively free the desired appropriate amplification product from nonspecific contaminants.

Tissue DNA Preparation:

TG avoid tedious and inefficient procedures for DNA isolation by directly proceeding to nucleic acid amplification with minimal tissue handling. The greatest time saving measure is the avoidance of DNA precipitation which in many protocols requires overnight incubation and at least two repeat steps. Use of tissue directly is based on the understanding that tissue DNA is required only for the initial amplification cycles to generate adequate amounts of DNA for subsequent amplification. The tissue sample needs only to be optimally treated to render its DNA available for initial amplification. By properly preparing the topographic sample for direct use in the amplification reaction an enormous savings in time and cost is realized.

Effective DNA amplification is the determining step for successful genotyping. The creation of a storage unit which results in a suspension of tissue particles of differing size and character is essential to amplifiability. In addition pretreatment steps as outlined below cause the topographic sample to become further effectively amplified. For the majority of cases pretreatment protocol 1 proves sufficient. In rare instances inclusion of protocols 2 and 3 in that order meet the need for effective amplification. Of importance in these protocols is minimal sample manipulation for ease and timeliness of application.

Conditions have been optimized and simplified for DNA extraction while avoiding tedious nucleic acid precipitation. The procedure is rapid and easy to perform with excellent reproducibility and high efficiency for clinical practice and research purposes. Specimens can sit overnight or up to a week at room temperature in the Topographic lysis buffer (TLB) 1 without any detriment allowing topographic sampling to be done at other facilities and mailed (at room temperature) to a central laboratory for further processing. Shorter incubations with higher concentrations of Proteinase K in TLB2 are equally effective, but overnight digestion has been found logistically to be the most convenient. Optimization of the Proteinase K concentration with the incubation time is critical. If the Proteinase K is too concentrated or the incubation time is too long, the Proteinase K will digest the DNA that is of interest to be amplifying. Conversely a shorten incubation time or not as concentrated and the Proteinase K will not digest proteins sufficient to render the DNA available. Tissue sampling tends to take place through the day and the sample filled tubes become available in the later afternoon for TLB mix adjustment. Following overnight digestion, the specimens are heated (99° Centigrade for 10 min.) and spun 2 min. in the morning at which time they are then ready for the amplification process or freezer storage.

Protocol 1: Topographic Sample Preparation, Initial Treatment

REAGENTS: Topographic Lysis Buffer 1 (100 mM NaCl, 25 mM EDTA pH 8.6, 10 mM Tris pH 8.3, 0.5% $NP_{40}$), and Topographic Lysis Buffer 2 (Proteinase K 2 mg/mL).

INSTRUMENTATION: Microcentrifuge, pipettors and pipettes, water bath, −20° C. freezer, 4° C. refrigerator, tube racks, tube floats, thermal cycler.

Approximately 0.50 cm$^2$ of tissue requires 95 μl of Topographic Lysis Buffer 1 and 5 μl of Topographic Lysis Buffer 2. To determine appropriate final volume of buffer mix, use following methods: (1) estimate tissue scrapped off slides; (2) make comparable standards (scrape known quantities 0.50 cm$^2$, 0.25 cm$^2$ etc. into 25 μl TLB1.); or (3), experience. Samples are variable, but Topographic Genotyping system is very tolerant of small judgment errors. Specimens can sit up to a week in Topographic Lysis Buffer 1 without any detriment. Topographic Lysis Buffer 1 (TLB1) is 95% and Topographic Lysis Buffer 2 (TLB2) is 5% of total volume of Topographic Lysis Buffer Mix (TLBM). Remember 25 μl of Topographic Lysis Buffer 1 is already in sample tubes.

Add Topographic Lysis Buffer 1 and 2 to labeled tubes post-topographic selection (tissue in 25 μl TLB1). Example, 0.5 cm$^2$ requires additional 70 μl Topographic Lysis Buffer 1 and 5 μl Topographic Lysis Buffer 2, 0.25 cm$^2$ requires 22.5 μl TLB1 and 2.5 TLB2 for total volume of 50 μl. Additions are proportional.

Samples adjusted in TLB mix in step 1 are placed in a float in 42° C. water bath for approximately 18 hr (overnight) for further digestion to extract DNA.

Tubes are removed and heated to 99° C. for 10 min. (thermal cycler or water bath) to deactivate TLB2 Proteinase K and also to further disrupt cross linking of proteins.

Spin 2 min. at 12,000 rpm's (table top centrifuge) to pellet undigested proteins and membranes. Not every tube will have a pellet. Tubes are stored in −20° C. freezer in labeled boxes in freezer racks and are ready for aliquoting into PCR reaction tube for DNA analysis.

DNA can be stored indefinitely. Specimen can be thawed, aliquots removed, and returned to freezer repeatedly for genetic analysis until depleted. Typically over 30 separate aliquots can be drawn off for PCR reactions. After depletion, up to 20 μl H$_2$O can be added and mixed in storage tube to wash DNA stuck on sides of tube into solution with H$_2$O. This sample can then be used successfully in more PCR reactions.

Protocol 2: Topographic Sample Preparation, Second Treatment-phenol Chloroform Treatment Unlike traditional Phenol/Chloroform treatment protocols, there is no ethanol precipitation step in which a DNA pellet is formed, dried (ethanol evaporated) and another step where fluid usually water is added to rehydrate the DNA pellet. Here, the sample remains in the same storage vial suspended in it's TLB mix and there is no change on the size of aliquot used in amplification protocol.

REAGENTS: Phenol:Chloroform:Isoamyl Alcohol (25:24:1), Chloroform.

INSTRUMENTATION: microcentrifuge, pipettors and pipettes, −20° C. freezer, 4° refrigerator, tube racks.

Phenol Chloroform treatment starts at any step post overnight incubation in TLB mix, It can be done either before or after heating, centrifuging, or freezing storage steps. (Phenol deactivates Proteinase K). If this step is performed post overnight incubation,the heating step performed normally is not necessary because Phenol deactivated Proteinase K.

Equal volume of Phenol:Chloroform:Isoamyl Alcohol (25:24:1) is added to volume of sample in tube, mixed vigorously to a cream color, then spun 30 sec. at 14,000 rpmŌs in centrifuge (room temp.) to separate aqueous phase (DNA in TLB mix) from Phenol phase (bottom) and interphase of proteins, membranes and other cell debris.

Open and draw off aqueous layer (DNA in TLB mix) into a new labeled tube discarding interface and phenol layer. Repeat step 1 and 2 again if necessary (rare).

Add equal volume of Chloroform, vortex 5 sec. and spin 30 sec. at 14,000 rpmōs in centrifuge (room temp.). Draw off top aqueous layer from bottom Chloroform and add to new labeled tube. Repeat step 3 if there is any question of contamination of sample with Phenol (rare). Sample is ready for usual aliquoting to PCR reaction tube or freezer storage.

Protocol 3: Topographic Tissue Preparation, Third Treatment-removal of Short Length DNA Fragments In a small minority of cases, topographic sample amplification proves ineffective following proteinase and phenol-chloroform treatment. Under these circumstance it is possible to effect nucleic acid amplification by filter separation of short length fragments of DNA. This effect is likely related to excessive nucleic acid breakdown in the same related to tissue breakdown prior to fixation, fixative effect, and or prolonged storage. These short DNA fragments may exert their negative effect on nucleic acid amplification by nonspecific triggering of the amplification reaction. Use of the filter is a simple step and does not involve tedious transferring of small liquid volumes.

The storage unit cellular suspension having been treated with proteinase K and phenol-chloroform is transferred into a Amicon centricon microtube filter system designed to produce a residual retentate of 25 microliters in which short DNA fragments less than 100 base pairs long has been permitted to pass through.

The sample is centrifuged until an appropriate retentate is produced. The sample may aliquoted for nucleic acid amplification or stored in this form.

Nucleic Acid Amplification:

Nucleic acid amplification is carried out over 36 cycles in a 48 μl volume. Sufficient product is generated to avoid need for internal nested primer amplification which carries a significant risk of contamination. Nucleic acid amplification is preferably carried out in a completely separate room away from the location where DNA sequencing is performed.

Optimal preliminary treatment of the tissue in the storage vial is critical to successful amplification of fixative treated DNA. Critical to tissue preparation is proper lysing of cell and nuclear membranes followed by appropriate protein digestion. Adjusting the PCR cycling parameters to favor poor quality DNA of fixative treated tissues is also critical for reliable results. Also valuable is careful addition of amplification enzyme at high temperature to minimize non-specific amplification triggered by misplaced primer fragments. By careful handling of the storage tube it is possible to carry out numerous DNA sequence analysis in parallel from minute tissue targets.

Protocol: Nucleic Acid Amplification of Topographic Samples

PRINCIPLE OF TEST: Area of selected gene is amplified from aliquot of storage sample by enzymatic nucleic acid amplification using primers (approx. 20 mer oligonucleotide) designed to hybridize to specific regions of the gene of interest.

REAGENTS: H$_2$O, MgCl$_2$, dNTP mix (A, G, C. & T are mixed in equal volumes), primers, Taq polymerase, molecular biological grade mineral oil, Sample DNA from extraction procedure.

INSTRUMENTATION: Thermal cycler, dry bath (78° C.), mini centrifuge, mixer, pipettors and tips, tube racks, permanent marker, tube opener, 4° C. refrigerator, −20° Freezer.

Preparation of PCR mix and high temperature amplification onset format on the thermal cycler is done in a separate Pre-PCR lab to avoid contamination with amplified products in the Post-PCR lab. Use ultraviolet light when hood is not in use to break down DNA contamination. Amplification reactants mixing and aliquoting is done in hood. It is not necessary to work under a hood as long as work area is completely free from even aerosolized amplified products contaminants. After high temperature onset, the amplification reaction tubes are closed tight, cycled then removed to the Post amplification lab to be opened.

2. Remove buffer #2, dNTP's, and primers from −20° freezer to thaw. Remove $H_2O$ and $MgCl_2$ from 4° C. refrigerator. Mix gently and briefly centrifuge. Mineral oil is stored in hood. Turn on dry bath to heat.

3. Label 1.5 mL tubes for mixes. Each amplification reaction has its own Mix 1 tube labeled with its gene-exon. Mix 2 is unvarying (may be combined with one or more genes; when total volume is 1000 µl, split in two).

For formalin fixed tissue, cytology filter arcs and cytospin samples use following Mix 1: 18.5 µl $H_2O$ 3.5 µl Buffer #2

7 µl $MgCl_2$ 0.5 µl of each primer.

For cytology fluids, cell lines and fresh/frozen samples use the following variation of Mix 1: 23.5 µl $H_2O$ 3.5 µl Buffer #2

2 µl $MgCl_2$ 0.5 µl of each primer.

All samples use Mix 2: 6.5 µl $H_2O$ 1.5 µl Buffer #2

3 µl $MgCl_2$

4 µl dNTPs mix (added later 0.25 µl Taq Polymerase)

Place reagents on ice after their addition to the mixes and return to freezer as soon as possible.

4. Line storage samples in row of tube rack according to desired order. Add 30 µl Mix 1 to each empty tube.

5. Add sample (filtered tips to avoid aerosol contamination) to corresponding tube. Formalin fixed tissue, cytology blocks and cytospin samples in LB/PK are mixed and 3 µl aliquoted out from bottom of tube (avoid pellet and floating debris). Cell lines and fresh/frozen samples in LB/PK are mixed and 1 µl is aliquoted out from bottom of tube (avoid pellet). Filter arc is added and submerged. Cytology fluids are mixed and 5 µl aliquoted into a pink tube to signal biohazard. (If sample depleted, up to 20 µl of $H_2O$ can be added, mixed in storage tube to wash DNA from sides and used successfully in PCR reaction.

6. Overlay reaction tubes with 2 drops (30 µl) mineral oil, close and label with PCR run and sample # Label "primer only" tube with PCR # (negative control).

7. Tubes are placed in Thermal Cycler with times programmed as described below. Block will heat to 99° C. for 5 min. count down. Taq is now removed from freezer and added to Mix 2, then mixed and centrifuged Return reagents to freezer and refrigerator. With 2 min. left in countdown, set Mix 2 in dry bath at 79° C.

8. After beep, Block will cool to 94° C. for 5 min. count down. All tube lids are opened and 15 µl of Mix 2 are added to bottom, under mineral oil layer. Tubes are sealed and PCR lid shut. Cycling proceeds as programmed below.

9. After cycling has ended, block is at 4° C. Remove sealed tubes to sequencing lab for agarose electrophoresis. Store in 4° C. for short time, or −20° C. long term storage. Turn off PCR machine.

File a Linked to:

File: 99° C., 5 min., 1 cycle.

File: 94° C., 5 min., 1 cycle.

File: 98° C., 30 sec.; 55° C., 1 min.; 72° C., 3 min., 1 cycle.

File: 94° C., 1 min.; 55° C., 1 min.; 72° C., 5 min., 15 cycle.

File: 94° C., 1 min.; 55° C., 1 min.; 72° C., 10 min., 20 cycles.

File: 72° C., 15 min., 1 cycle.

File: 4° C. soak.

To achieve specific and high yield gene amplification, delay addition of Taq polymerase until the entire reaction mixture is held at 94° C. This "hot start" is accomplished with addition of heated (79° C.) Mix 2. Follow addition of Taq Polymerase with a further high temperature ramp step of 30 seconds at 98° C. for the first amplification cycle is important. This additional high temperature helps to overcome covalent bonding and limitation in motion related to fixation of tissue proteins and nucleic acids. Allow longer times for individual steps. Avoid rapid ramping steps or shortened programs which have the undesirable effect of encouraging nonspecific product amplification at the expense of specific target gene amplification.

Amplicon Isolation and DNA Sequencing:

Agarose gel electrophoresis accomplishes two purposes. First it allows separation of oligonucleotide primers and other small sized nonspecific amplification product to be cleanly separated from amplicon. The isolation of pure true amplicon is essential for clean DNA sequencing. Second it enables evaluation of efficiency and specificity of amplification. The latter is important in Quality Assurance and Control. Failed individual reactions may be repeated or undergo Phenol/Chloroform and filtering of short length DNA fragment treatment (see above).

Horizontal agarose electrophoresis is performed in standard fashion. TG produces sufficient desired product for a variety of DNA structural analyses including direct DNA sequencing. The latter, which results in detailed sequence information for comparative analysis is easily performed by standard protocols which isolate the amplified product form agarose following by sequencing reactions such as dideoxy chain termination. Sufficient specific product is produced to enable repeated structural or sequence analyses from a single round of nucleic acid amplification.

Once amplified DNA has been obtained from the minute tissue sample, screening or specific detection of DNA can be performed to identify and characterize mutational damage. The most detailed analysis involves direct DNA sequencing which is usually performed using dideoxy chain termination and sulfur-35 radiolabelled nucleotide incorporation. (Sanger F, Nicklen S, Coulson A R, DNA Sequencing with Chain-Terminating Inhibitors. Proc. Natl. Acad. Sci. USA, 74:5463–5467, 1977), incorporated by reference. TG provides sufficient amplified DNA so that these procedures may be carried out under established standard conditions with high success. The most convenient format for clinical application would involve purification of amplified DNA from agarose followed by direct sequencing. The overall process from tissue receipt, histopathologic evaluation, target selection and topographic sampling, storage unit treatment, nucleic acid amplification and DNA sequence determination can be conveniently followed by the following computerized information system.

Informatics

TG consists of a series of simple methodological steps beginning with tissue histology, proceeding through DNA amplification and mutational analysis and concluding with integration of morphologic and genetic information. The process of TG is broken down into parts in which several interrelated steps are performed by the technologist or pathologist/scientist. These parts usually consists of parallel manipulation of several individual specimens at the same time in order to achieve a significant savings in time and cost. Once a specimen has been accessioned and entered the TG analysis, the performance of individual technical components is performed blindly without knowledge concerning the biological significance of an individual sample. All specimens are therefore handled in an identical fashion thereby avoiding introduction of bias. Only at the conclusion of the analysis, when integration of morphologic and genetic data is carried out, can the full significance of the individual sample made aware. To coordinate this effort an informatics system has been developed based upon the specific aspects of TG which functions to inform the user the progress and results of an single or groups of specimen samples.

This informatics program consists of a relational database which interrelates clinical, histopathologic, and genetic information (Table 3). TG informatics operates on eight levels of relationships consisting of over 75 fields which can be further configured to suit the individual needs of a particular user. This informatics database is very important in maintenance of quality control and assurance over the myriad activities of different parts of the analysis. The database also provides the means to determine trends and patterns in the integrated histopathologic and genetic information. For example the presence of certain genetic alterations in specific forms of human cancer can be made evident by analysis using the database and the statistical significance tested.TG informatic relational database is an essential component enabling the user to keep in touch with ongoing analysis, define genetic trends and maintain operating control.

As a further example, if a new cancer related genetic alteration is discovered, TG utilizes specific DNA sequence information to formulate appropriate nucleic acid amplifying primers and sequencing primers with which to identify and characterize the genetic mutation. TG allows the user to access any archival tissue specimens to best evaluate the significance of this potentially important genetic alteration. In and of itself this is of enormous advantage as the user is not restricted to large quantity fresh or fresh-frozen tissue for testing. Instead the user could subject selected archival topographic specimens that have already been evaluated for genetic alterations. TG has the distinct attribute through the creation of storage units to create a bank of readily available topographic samples circumventing the need to continuously recut tissue blocks for every new gene analysis. These storage units will already have been analyzed and therefore the new gene in question can be studied in the context of associated genetic alterations on that specimen. In this way TG would have broad applicability greatly enhancing the information obtained to achieve assess in a more rapid fashion the significance of a newly identified genetic alteration.

The informatics programs outlined in Table 3 can be very easily integrated with existing national, regional and local cancer registries. For example, patients with particular forms of cancer that have proven resistant to a newly introduced chemotherapy can be compared to patients with similar forms of cancer that exhibited a good response. The broad applicability of TG would be ideal for such an analysis by its capacity to be effective on virtually any archival fixed tissue specimen irrespective of size or storage age.

The informatics program to support TG is outlined in Table 3. This application utilizes direct sequencing of the amplified DNA to detect and characterize point mutational damage. In this format tissue histology, amplification, amplified product purification and DNA sequencing is coordinated by the informatics program as shown. The specific genetic targets currently being performed by TG is outlined in Table 3. This list is an under representation of the applicability at this time as many more genetic targets could be incorporated in the analysis. TG provides a means whereby new gene discoveries could be quickly brought to the clinical bedside and research laboratory.

TABLE 3

INFORMATICS: OVERALL ORGANIZATION

| RELATIONAL LEVEL | FOCUS | NUMBER FIELDS |
|---|---|---|
| 1 | PATIENT | 6 |
| 2 | TISSUE | 10 |
| 3 | SPECIMEN | 7 |
| 4 | STORAGE UNIT | 9 |
| 5 | GENE | 25 |
| 6 | PCR AMPLIFICATION | 8 |
| 7 | SEQUENCING GEL | 9 |
| 8 | GENOTYPE | 4 |

LEVEL 1: PATIENT RELATED DATA

| TITLE | ABBREVIATION | FIELD TYPE |
|---|---|---|
| LAST NAME | PT_LAST | TEXT |
| FIRST NAME | PT_FIRST | TEXT |
| MIDDLE INITIAL | PT_MID | TEXT |
| SOCIAL SECURITY NO. | PT_SSN | NUMBER |
| BIRTH DATE | PT_BIRTH | DATE |
| SEX | PT_SEX | TEXT |
| COMMENT | PT_CON | TEXT |

LEVEL 2: TISSUE RELATED DATA

| TITLE | ABBREV | FIELD TYPE |
|---|---|---|
| SITE | TS_SITE1 | TEXT |
| ADDITIONAL SITE DESCRIPTION | TS_SITE2 | TEXT |
| CELL | TS_CELL1 | TEXT |
| ADDITIONAL CELL DESCRIPTION | TS_CELL2 | TEXT |
| HISTOPATH | TS_HIST1 | TEXT |
| ADDITIONAL HISTOPATH DESCRITION | TS_HIST2 | TEXT |
| PROGRESSION | TS_PROG1 | TEXT |
| ADDITIONAL PROGRESSION DESCRIPTION | TS_PROG2 | TEXT |
| PROJECT | TS_PROJ | TEXT |
| COMMENTS | TS_CON | TEXT |

LEVEL 3: SPECIMEN RELATED DATA

| TITLE | ABBREVIATION | FIELD TYPE |
|---|---|---|
| DATE SPECIMEN TAKEN | SP_DATE | DATE |
| PT AGE WHEN SPECIMEN TAKEN | SP_PTAGE | NUMBER |
| HOSPITAL | SP_HOSP | TEXT |
| ACCESSION NUMBER | SP_ACCNO | TEXT |
| BLOCK DESIGNATION | SP_BLOCK | TEXT |
| TOPOGRAPHIC SITE | SP_TOP | TEXT |
| FIXATION | SP_FIX | TEXT |
| COMMENT | SP_CON | TEXT |

TABLE 3-continued

LEVEL 4: STORAGE UNIT

| TITLE | ABBREV | FIELD TYPE |
|---|---|---|
| STORAGE LOCATION | ST_LOC | TEXT |
| DATE TOPOGRAPHIC SELECTION | ST_DATE | DATE |
| TOPOGRAPHER | ST_OPNA | TEXT |
| NO. RECUTS USED | ST_NORC | NUMBER |
| NO. RECUTS UNDEPARAFFINED LEFT | ST_NOUND | NUMBER |
| NO RECUTS DEPARAFFINED LEFT | ST_NODEP | NUMBER |
| NO. POST-TOPOGRAPHIC SLIDES LEFT | ST_NOPTT G | NUMBER |
| STORAGE UNIT TREATMENT | ST_TREAT | TEXT |
| COMMENTS | ST_CON | TEXT |

LEVEL 5: INDIVIDUAL GENE DATA

| TITLE | ABBREVIATION | FIELD TYPE |
|---|---|---|
| H-RAS-1 EXON 1 | GE_HRAS_01 | TEXT |
| H-RAS-1 EXON 2 | GE_HRAS_02 | TEXT |
| D2S123 | GE_D2S123 | TEXT |
| A1AT EXON 2 | GE_A1AT_02 | TEXT |
| A1AT EXON 3 | GE_A1AT_03 | TEXT |
| A1AT EXON 5 | GE_A1AT_05 | TEXT |
| GLUCOCEREBROSIDASE EXON 2 | GE_GCS_02 | TEXT |
| GLUCOCEREBROSIDASE EXON 9 | GE_GCS_09 | TEXT |
| GLUCOCEREBROSIDASE EXON 10 | GE_GCS_10 | TEXT |
| K-RAS-2 EXON 1 | GE_KPAS_01 | TEXT |
| K-RAS-2 EXON 2 | GE_KPAS_02 | TEXT |
| N-RAS EXON 1 | GE_NRAS_01 | TEXT |
| N-RAS EXON 2 | GE_NRAS_02 | TEXT |
| P53 IMMUNOHISTOCHEMISTRY | GE_P53IMM | TEXT |
| P53 EXON 5 | GE_P53_01 | TEXT |
| P53 EXON 6 | GE_P53_06 | TEXT |
| P53 EXON 7 | GE_P53_07 | TEXT |
| P53 EXON 8 | GE_P53_08 | TEXT |
| MTS1 EXON 2 (PROX 1/3) | GE_MTS_02A | TEXT |
| MTS1 EXON 2 (MID 1/3) | GE_MTS_02B | TEXT |
| MTS1 EXON 2 (DIST 1/3) | GE_MTS_02C | TEXT |
| C-RAF-1 EXON 15 | GE_RAF_15 | TEXT |
| C-RET EXON 7 | GE_RET_07 | TEXT |
| C-RET EXON 8 | GE_RET_08 | TEXT |
| HUMANPAPPILOMAVIRUS | GE_HPV | TEXT |

LEVEL 6: NUCLEIC ACID AMPLIFICATION DATA

| TITLE | ABBREVIATION | FIELD TYPE |
|---|---|---|
| PCR ACCESSION NUMBER | PCR_ACCNO | NUMBER |
| PCR OPERATOR | PCR_OP | TEXT |
| PCR DATE PERFORMED | PCR_DATE | DATE |
| PCR METHOD | PCR_METH | TEXT |
| UPSTREAM PRIMER | PCR_UP | TEXT |
| DOWNSTREAM PRIMER | PCR_DOWN | TEXT |
| PCR RESULT | PCR_RSLT | TEXT |
| COMMENT | PCR_COM | TEXT |

LEVEL 7: SEQUENCING GEL INFORMATION

| TITLE | ABBREVIATION | FIELD TYPE |
|---|---|---|
| GEL ACCESSION NUMBER | GEL_ACCNO | NUMBER |
| GEL OPERATOR | GEL_OP | NAME |
| GEL DATE PERFORMED | GEL_DATE | DATE |
| SEQUENCING METHOD | GEL_SEQ | TEXT |
| GEL METHOD | GEL_METH | TEXT |
| SEQUENCING PRIMER | GEL_PRIM | TEXT |
| RADIONUCLEOTIDE LABEL | GEL_LAB | TEXT |
| SEQUENCING RESULT | GEL_RSLT | TEXT |
| COMMENT | GEL_CON | TEXT |

LEVEL 8: GENOTYPING DATA

| TITLE | ABBREVIATION | FIELD TYPE |
|---|---|---|
| SIGNIFICANCE | TG_SIG | TEXT |
| BASE RESULT | TG_BASE | TEXT |
| AMINO ACID RESULT | TG_AA | TEXT |
| ZYGOSITY & ALLELIC LOSS | TG_ZYG | TEXT |

Informatics Database Templates

Arrangement of Fields for Comparative Data Analysis

Lookup an Individual Patient Genotyping Results:
NAME¦SSN¦TISSUE PROJECT¦HOSPITAL¦ACCESSION NUMBER¦BLOCK DESIGNATION¦TOPOGRAPHIC SITE¦STORAGE LOCATION¦PCR NO.¦PCR RESULT¦GEL NO.¦GEL RESULT¦GENE¦SIGNIFICANCE¦BASE RESULT¦AMINO ACID RESULT¦ZYGOSITY Planning Specimen Sampling:
TISSUE PROJECT¦HOSPITAL¦ACCESSION NUMBER¦BLOCK DESIGNATION¦TOPOGRAPHIC SITE¦DATE SPEC. TAKEN¦PT AGE WHEN SPEC TAKEN¦FIXATION¦SPECIMEN COMMENTS¦NO. RECUTS UNDEPARAFFINIZED LEFT Setup for Topographic Selection:
STORAGE LOCATION¦TISSUE PROJECT¦HOSPITAL¦ACCESSION NUMBER¦BLOCK DESIGNATION¦TOPOGRAPHIC SITE¦NO. RECUTS USED¦NO. RECUTS DEPARAFFINIZED LEFT¦NO. POST-TOPOGRAPHIC SLIDES LEFT¦STORAGE COMMENTS PCR Setup:
GENE¦TISSUE PROJECT¦STORAGE LOCATION¦PCR ACC. NO.¦PCR OPERATOR¦PCR DATE¦PCR METHOD¦UPSTREAM PRIMER¦DOWNSTREAM PRIMER¦PCR COMMENTS PCR Review:
PCR NO.¦PCR RESULT¦GENE¦LAST NAME¦SSN¦ORGAN SITE¦HISTOPATHOLOGY¦TISSUE PROJECT¦HOSPITAL¦ACCESSION NUMBER¦BLOCK DESIGNATION¦TOPOGRAPHIC SITE¦STORAGE LOCATION¦GEL ACC. NO.¦GEL RESULT¦BASE RESULT¦AMINO ACID RESULT¦ZYGOSITY¦PCR COMMENTS Sequencing Gel Setup:
GENE¦TISSUE PROJECT¦STORAGE LOCATION¦GEL ACC. NO.¦GEL OPERATOR¦GEL DATE¦SEQUENCING METHOD¦GEL METHOD¦SEQUENCING PRIMER¦RADIONUCLEOTIDE LABEL¦GEL COMMENTS Sequencing Gel Review:
GEL ACC. NO.¦GEL RESULT¦PCR NO.¦GENE¦LAST NAME¦SSN¦ORGAN SITE¦HISTOPATHOLOGY¦TISSUE PROJECT¦HOSPITAL¦ACCESSION NUMBER¦BLOCK DESIGNATION¦TOPOGRAPHIC SITE¦STORAGE LOCATION¦PCR RESULT¦BASE RESULT¦AMINO ACID RESULT¦ZYGOSITY¦GEL COMMENTS Tissue/Gene Analysis:
ORGAN SITE|ADD. ORGAN SITE|CELL TYPE|ADD. CELL TYPE|HISTOPATH|ADD. HISTOPATH|PROGRESS|ADD. PROGRESS|TISSUE PROJECT|GENE|SIGNIFICANCE|BASE RESULT|AMINO ACID RESULT|ZYGOSITY Status of Cases in Progress: PCR NO.|PCR RESULT|GEL NO.|GEL RESULT|TISSUE PROJECT|GENE|SIGNIFICANCE|BASE RESULT|AMINO ACID RESULT|ZYGOSITY States of Tissue Project:
TISSUE PROJECT|NAME|HISTOPATH|HOSPITAL|ACC. NO.|GENE|SIGNIFICANCE|BASE RESULT|AMINO ACID RESULT|ZYGOSITY Application of Topographic Genotyping TG is designed to enable fixative treated tissue specimens to be sampled in minute detail according to microscopic cellular characteristics so that the genetic analysis for specific DNA damage is focused on the histopathologic properties of that unique tissue sample. TG integrates genetic and histopathologic analysis in a simple, timely, cost and includes a compatible relational database to track individual and groups of specimens and to evaluate aspects of quality control and assurance in a format suitably adapted for clinical application. With TG, the vast archive of fixative treated, paraffin-embedded tissue specimens becomes available for retrospective integrated genetic/histopathologic analysis. TG is equally effective irrespective of archival age or specimen size and as such may be expected to have very broad application. The use of TG is outlined in Table 4 and described below. The user of TG is free to investigate any tissue specimen for precise DNA sequence alterations.

MOLECULAR ONCOLOGY: Since the initial recognition of specific DNA coding mutational damage affecting certain oncogene and tumor suppresser genes, the list of such altered genes involved in human cancer has grown each year. Many currently studied genes consist of those shown Table 4 and may be expected to increase in number rapidly over time. TG provides the means whereby clinical tissue specimens may be critically evaluated for these important cancer related gene alterations.

The user of TG would decide upon a specific gene of interest to study for DNA structural alterations. He/she could consult any of a number of readily available repositories of genetic information such as GenBank, European Molecular Biology Library (EMBL), or other gene sequence database service. In addition to the sequence of the gene of interest such service provides information on gene structure including intron/exon splice sites, location of specific cancer related mutational damage and corresponding RNA and protein alterations. Alternatively, published manuscripts may be consulted for genetic sequence information of the oligonucleotide primers utilized to study a specific gene target. Such information is all that is required to evaluate the presence, frequency, and significance of cancer related mutational injury. Amplification from fixative treated tissue is best limited by amplicon length to approximately 200 base pairs. Oligonucleotide primers would be fashioned based on genetic sequence information to center the amplification on the anticipated site of genetic damage. These oligonucleotide primers would be utilized for both DNA amplification and subsequent sequencing for detection and precise characterization of mutational damage. The specificity of amplification would be confirmed by matching of provided DNA sequence information to that derived from the tissue specimen being evaluated.

Having appropriate oligonucleotide primers for the specific gene of interest TG would enable to the user to evaluate informative tissue specimens for relationship to human cancer development and progression. At present the limitations incumbent upon the use of large fresh tissue specimens prevents analysis of optimal specimens for genetic study. TG would broaden the range of specimens available for evaluation thereby attaining critical information at a much faster rate than that currently in practice. For example to determine whether a specific DNA sequence alteration was in fact predictive of degree of tumor aggressive or treatment responsiveness, recourse may be easily had to a tissue inventory in which specimens over 5 or 10 years in age are recorded from patients who have been followed forward from that time. Such correlated tissue inventories are available from national, regional and local cancer registries whose function is to collate this type of follow-up information. The tissues in such registries is almost invariably fixative treated and for many cancers would include minute sized specimens such as that obtained from biopsy sampling. Registries of this type are currently reluctant to provide specimens freely for molecular analysis since current approaches result to total destruction of the tissue. TG would provide the means to use sparing amounts of such fixative treated tissues to yield critical genetic information. By more carefully selecting the tissue specimens from highly informative subjects which most critically evaluate a specific hypothesis, TG becomes the most effective means to attained causally related and predictive genetic information.

In addition to DNA coding mutational damage, TG can inform the user of the presence of gene allelic loss by examination of loss of heterozygosity. Loss of heterozygosity analysis (LOH) is an established genetic method in which the absence of one or both alleles from a tissue of interest is detected (Murphee A L, Benedict W F, Retinoblastoma: Clues to Human Oncogenesis. Science 223:1028–1033, 1985), incorporated by reference. Currently LOH is usually accomplished by restriction fragment length polymorphism analysis which requires relatively large sample size. TG, using nucleic acid amplification of microsatellite regions of DNA (Weissenbach J, A Second Generation Linkage Map of the Human Genome Based on Highly Informative Microsatellite Loci. Gene, 135:275–278, 1993), incorporated by reference, in proximity to genes lost during cancer progression, may be used to determine loss of heterozygosity. For loss of heterozygosity analysis by TG a sample of normal tissue and a separate sample to tumor tissue would be analyzed. The loss of one or both alleles from the tumor sample would indicate loss of genetic material in relationship to cancer growth and progression. At present, loss of heterozygosity determination is very often confounded by the fact that obtaining a large tissue specimen based on gross appearance only in the fresh state very often results in the undesired inclusion of normal tissue elements in significant amounts. TG avoids this complication by optimized purity of tissue elements in the sample based on careful histopathologic and topographic considerations which control sample selection for genetic analysis. As described in the section on topographic sampling from glass slides, even when tumor is seen to infiltrate between normal cellular elements, by judicious wetting and scraping using the scalpel point it is possible to cleanly separate tumor from normal for selection of pure tumor sample. In this way it is possible not only to detect point mutational damage but to comment on the presence or absence of allelic loss.

TG for microsatellite analysis is one area of great potential as the number and location of microsatellites is very rapidly increasing due to the work of the Human Genome Project to fully map human DNA according to position of individual microsatellites. Genomic information sources such as GenBank may be electronically consulted for up to the minute detailed microsatellite maps and corresponding primer sequences upon which to base a loss of heterozygosity analysis for virtually any part of the human genome.

INHERITED GENETIC DISEASES: TG, by virtue if its capacity to effectively analyze archival fixed tissue, would be of enormous value in the diagnosis and characterization of inherited diseases. The list of genetic disease with known mutational change is enormous and expanding on a daily basis. Repositories of such information of major texts on the subject can be consulted through most of the network communication services such as Medline. Detection of these diseases is usually performed on a blood or other easily obtainable tissue sample such as skin. There are many instances however where this easy availability is not possible such as in the case when suspected family members are no longer alive. In these instances there may well be archival formalin fixed, paraffin embedded tissue specimens stored as an archival fixative treated tissue specimen in a hospital laboratory. TG would represent the means to effectively analyze such tissue for informative genetic alterations.

TG would provide genetic information upon which to construct family tree type inheritance patterns in turn greatly increasing our general understanding of inherited genetic disease. Once a suspected genetic alteration was found in certain family members to be altered, recourse can be had to archival specimens to further evaluate the inheritance pattern of DNA sequence alterations prior to more broad based investigation of living family members. In this way a strong basis for the presence and type of genetic alterations can be achieved before living family members are involved in the evaluation. By searching archival tissue registries such as those available in most hospitals by specific clinical terminology, tissues from patients suspected for variants patterns of genetic disease may be identified and studied for their relationship to established disease states. TG expands the range of genetic analysis to include a broader cross section of patient tissue specimens better able to discover new and evaluate the role of specific genetic alterations.

GENETIC POLYMORPHISM DETERMINATION: In a similar fashion, TG can utilize microsatellite and genetic sequence polymorphism anaylsis as a tissue typing system for identification of individual subjects. Unique genetic markers would serve as the basis to clearly indicate that a specific tissue specimen in fact originates for a specific individual. This is of great value as a quality assurance measure in standard histopathology practice as it is not uncommon for small tissue specimens from one person may inadvertently contaminate the tissue specimens of another person. TG, being effective on fixative treated tissue specimens of small size, would represent the only means to specifically identify person of origin.

To accomplish this type of tissue identification, the user of TG would search genetic data banks for informative regions of the human genome for individual polymorphism. One such well established genetic targets are the HLA antigens, the genetic sequence of which has been detailed for use in individual identification (Klein J, O'Huigin C, Composite Origin of Major Histocompatibility Complex Genes. Current Opinion in Genetics and Development, 3:923–930, 1993), incorporated by reference. The frequency with which such HLA targets show variation in the human population have been described. Depending on the level of assurance desired, the user of TG would select one or more such targets for amplification. Identification can then be performed by direct sequencing or specific hybridization assay kits which are currently available. The feature of the storage unit in TG would enable the user to obtain up to 20 to 30 or more individual assays upon which to build a detailed tissue identification analysis with great assurance. Furthermore this would all be accomplished without unnecessary sacrifice of the tissue block specimen which may be critically needed for histopathologic evaluation.

TG could find similar use in forensic medicine when a need arises to relate a current tissue or blood specimen to that of an archival fixed tissue specimen. At present there is no effective means to consistently tissue type fixative treated material. TG would provide then means to genotype and identify archival fixed tissue for comparison to other fresh or fixed tissue specimens.

INFECTIOUS DISEASES: TG is of enormous value in the diagnosis and characterization of microbial infection. Molecular methods currently are being applied to the detection of microbial infection but in general requires a sizable fresh tissue specimen to be effective. TG would enable molecular detection to be focused on the exact site or sites with a large complex tissue specimen wherein microorganisms may be expected to be found. Careful and precise selection of tissues for nucleic acid amplification would represent the key step to significantly improving our ability to achieve earlier detection of microbial infection. Tissue selection for microorganism detection would follow microscopic evaluation, building upon the insights gained through histopathologic analysis, and not compete with morphologic study for precious tissue specimens.

For example, a tissue specimen may first be subject to careful histopathologic analysis wherein one or more minute abscess sites may be found. Such site would not be appreciated or sampled when examining the gross specimen and therefore would be missed. Once found such minute abscess sites could be selectively sampled providing the enriched starting material for a nucleic acid/genotyping type of analysis for microorganism detection and characterization. The approach offered by TG is particularly attractive since at present there is no other means to effectively deal with such a condition of microscopically discovered infection.

Even more importantly, TG would provide detailed structural information of the nature of a specific offending organism. Since amplification could be directed at any known region of the organism information concerning mutational change or the presence of genomic virulence related factors would be available. TG would enable specific genotyping of microorganism based upon unique DNA content and therefore would represent an important ancillary with which to detect and follow microbial infection. To accomplish this purpose the user may consult microbial genome sequence data banks such as those available through the National Institutes of Health. The information provided would allow the construction of oligonucleotide probes designed to identify and characterized defined regions of the organism in question with particular emphasis on microbial virulence factors. By analyzing tissue specimens in a retrospective fashion from patients known to have pursued a certain course or to have exhibit a certain clinical pattern of treatment responsiveness, it becomes possible to use TG to establish the define the presence of new infectious agents or genotypes of microorganisms.

TABLE 4

APPLICATION OF TOPOGRAPHIC GENOTYPING

| APPLICATION | EXAMPLE |
| --- | --- |
| MOLECULAR ONCOLOGY | |
| POINT MUTATIONAL DAMAGE | ONCOGENE/ANITONCOGENE MUTATIONAL CHANGE |
| ALLELIC LOSS | MICROSATELLITE LOSS OF HETEROZYGOSITY |
| MICROSATELLITE INSTABILITY | MICROSATELLITE MARKER INSTABILITY |
| INHERITED GENETIC DISEASE | GERMLINE MUTATIONAL CHANGE STUDY OF ARCHIVAL TISSUES FOR FAMILIAL INHERITANCE STUDIES |
| POLYMORPHISM DETERMINATION | GENOMIC POLYMORPHISM DETERMINATION MICROSATELLITE ANALYSIS QUALITY CONTROL OF CONTAMINATION IN PATHOLOGY |
| INFECTIOUS DISEASES | |
| MICROORGANISM DETECTION | SPECIFIC MICROORGANISM DNA DETECTION |
| MICROORGANISM GENOTYPING | DNA BASED GENOTYPING |
| DETERMINATION OF VIRULENCE | GENOMIC CORRELATES OF VIRULENCE |
| VIRAL INTEGRATION | INTEGRATION RELATED DNA DETECTION |

TABLE 5

CANCER RELATED DNA CODING GENE ALTERATIONS

| GENE | GENE LOCATION | YEAR FIRST DISC | AFFECTED HUMAN CANCERS |
| --- | --- | --- | --- |
| K-RAS-2 | EXONS 1 & 2 | 1983 | COLORECTAL, LUNG, PANCREAS ADENOCARCINOMA |
| H-RAS-1 | EXONS 1 & 2 | 1983 | GENITOURINARY & SKIN CANCERS |
| N-RAS | EXONS 1 & 2 | 1985 | HEMATOLOGIC MALIGNANCIES |
| P53 | EXONS 5–8 | 1988 | MANY TYPES OF HUMAN CANCER |
| C-RET | EXONS 7 & 8 | 1988 | THYROID & ENDOCRINE CANCERS |
| MCC | SCATTERED | 1990 | COLORECTAL & OTHER ADENOCARCINOMAS |
| APC | SCATTERED & MUTATION CLUSTER REG. | 1990 | COLORECTAL & OTHER ADENOCARCINOMAS |
| C-RAF-1 | EXON 15 | 1993 | LUNG CANCERS |
| VEL | EXONS 1–3 | 1993 | RENAL CELL CARCINOMA VON HIPPEL LINDAU DISEASE |
| MTS1 | EXONS 1 & 2 | 1994 | MELANOMA & WIDE RANGE OF HUMAN CANCERS |

EXAMPLE OF USE OF TOPOGRAPHIC GENOTYPING

The most frequent application of Topographic Genotyping (TG) would be in the very common medical situation involving diagnosis and treatment of human cancer. As described below, TG would be used at several points throughout the patient course critically influencing clinical decision-making. There is at present no practical alternative means to obtain the information made available by TG which can be had at minimal cost in a timely fashion.

The patient with cancer would typically come to attention when a mass lesion would be detected either directly as a palpable nodule felt by the patient or indirectly by radiologic examinations performed in response to specific clinical symptoms or laboratory biochemical alterations. At this point, early in the clinical course, the main objective is to establish a firm diagnosis of the presence of cancer with minimal intervention delaying major surgery until it can be planned and carried out with greatest benefit. The usual practice is to obtain a small sized biopsy specimen from the suspected site of cancer formation and confirm the diagnosis by microscopic analysis. The small but vital nature of the tissues specimens at this point in clinical mamangement exclude most genetic analyses which consume relatively large amounts of tissue preventing traditional histopathologic diagnosis.

TG is designed to work off minute targets sites from fixative treated tissue specimens providing specific information on the presence and type of cancer related gene damage present in that cancer. This is accomplished without any sacrifice a tissue or histologic treatment. In fact the molecular analysis provided by TG complements histopathologic evaluation confirming the presence of cancer and indicating the degree of biological aggressiveness inate that individual tumor. The integrated histopathologic/genetic information can be used in certain circumstances at this early stage to predict pattern and extent of cancer spread prior to it having even occurred. Patients can be placed into clinical subsets with greater or lesser risk for malignant progression. Through the use of TG on small sized biopsy specimens the result is a more secure diagnosis of cancer and a better understanding of potential biological behavior on an individual case basis.

Once a decision to perform major surgery has been reached, TG would be intimately involved in the full laboratory analysis of the removed tissues. In the case of a mastectomy performed to excise a breast cancer, the first priority is to carefully and fully analyze the specimen for sites of cancer formation and spread and to characterize the malignancy according to traditional histopathologic features empirically known to predict tumor aggressiveness. Given the current emphasis on this disease and better methods for early diagnosis, many breast cancers are small in size. Despite the availability of a large tissue resection there still may be no fresh tissue remaining following histologic evaluation. More importantly detailed microscopic analysis is required in order to identify critical sites in the specimen where genetic analysis needs to be applied. For example there may be two distinct sites of cancer formation as well as three separate sites where atypical cellular proliferations are found in the breast resection. These areas could only be identified by histologic examination and could not be sampled by grossly observing the specimen. TG is designed to use morphologic clues to sample the tissue at precise points of biological importance. As a result TG would be the essential means to analyze this type of specimen for detailed genetic alterations in turn used to guide medical management.

Later in the patient's clinical course, it may come to pass that tumor may recur at a distant site such as the liver. Having a history of breast cancer, the occurrence would be highly suspicious for return of breast cancer. This would nevertheless have to be confirmed which would be accomplished by once again obtaining a representative piece of tissue. Given the circumstances the tissue specimen would invariably be small in the form of a biopsy to histologically confirm cancer recurrence. Once again standard molecular technique would not be suitable due to the minute size of the sample. TG would provide the means to analyze the specimen and compare the genetic alterations to that present in the previous tissue specimens. This typical scenario points out how at three separate time TG would be the only effective means to analyze the tissue on a typical case of human cancer.

Finally the storage capability of TG permitting up to thirty separate genetic tests on a single topographic sample would allow newly discovered genetic alterations to be studied on previously sampled tissue specimens without the need to recut the tissue block. As our understanding of genetics and cancer increases together with a better knowledge of the human genome, TG would be the mechanism to retrospectively analyze already removed tissue specimens in the most effective and cost efficient manner.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for topographic genotyping comprising the steps of:
   placing a biological specimen having DNA of a patient under a microscope;
   inspecting the biological specimen microscopically with the microscope;
   choosing a microscopic sized target on the biological specimen based on its histopathologic characteristics;
   separating the target from the specimen;
   extracting DNA from the target in an aqueous solution, wherein the extraction does not include DNA precipitation;
   centrifuging the aqueous solution from the extraction step directly from the DNA extracting step to create a pellet and a DNA-containing supernatant;
   removing the DNA-containing supernatant so that the DNA sequences therein can be amplified;
   amplifying the DNA sequences of the DNA-containing supernatant; and
   detecting mutations in the DNA sequences.

2. A method according to claim 1, wherein the biological specimen is fixative treated tissue.

3. A method according to claim 1, wherein the biological specimen is a tissue section, cytological fluid, filter or cellular specimen.

4. A method according to claim 1, wherein the specimen is a tissue section, and the separating step further includes slicing the target from the tissue section and placing the target on a glass slide.

5. A method according to claim 1, wherein the specimen is a tissue section, and the separating step further placing the target in a tube.

6. A method according to claim 1, wherein the separating step further includes cutting an arc segment from the specimen, and placing the segment in a tube.

7. A method according to claim 1, wherein the extracting step further includes placing the target in a lysis buffer.

8. A method according to claim 7, wherein the extracting step further includes contacting the target with proteinase K.

9. A method according to claim 7, wherein after placing the target in a lysis buffer, there is a step of adding phenol and chloroform into the lysis buffer with the target.

10. A method according to claim 9, wherein after the adding step, there is a step of separating short length fragments of DNA, wherein the DNA is less than 100 base pairs in length from the target.

11. A method according to claim 1, wherein the amplifying step comprises:
    choosing a primer corresponding to a gene of the patient;
    adding the primer to the DNA sequences; and
    performing polymerase chain reaction on the DNA sequences with primer.

12. A method according to claim 1, wherein the detecting step further includes determining the DNA sequence.

13. A method according to claim 12, further comprising comparing the determined DNA sequence with known DNA sequences for corresponding DNA regions of the target.

14. A method according to claim 1, further comprising the step of establishing whether the DNA sequence is associated with a cancer.

15. A method according to claim 1, further comprising the step of establishing whether the DNA sequence is associated with a condition hazardous to the health of the patient.

16. A method according to claim 1, wherein the amplifying step comprises cycling the DNA sequences in a polymerase chain reaction machine, with each cycle comprising a heating step to a temperature no greater than 99° C., and a cooling step to a temperature of 55° C. in 5 minutes.

17. A method according to claim 16, wherein the separating step includes a step of cutting one to three 2–6 μm thick histologic sections from the specimen.

18. A method according to claim 15, wherein the biological specimen is a human tissue specimen.

19. The method of claim 1, wherein thirty or less separate tests are performed on a single sample.

20. The method of claim 1, further comprising using the results of the genotyping in relational database.

21. The method of claim 20, wherein the database is used to identify a new type of cancer.

22. The method of claim 20, wherein the database is used to devise a treatment plan to treat a patient with diagnosed cancer.

23. The method of claim 22, wherein the cancer is selected from the group consisting of colorectal cancer, lung cancer, pancreas adenocarinoma, genitourinary cancer, skin cancer, hematologic malignancy, thyroid cancer, endocrine cancer, breast cancer, renal cell carcinoma, and von Hippel Lindau disease.

24. The method of claim 15, wherein the condition hazardous to the health of the patient is selected from the group consisting of inherited diseases, genetic polymorphisms, and infectious diseases.

25. The method of claim 1, comprising the further step of diagnosing an inherited disease in a patient.

26. The method of claim 1, comprising the further step of determining a genetic polymorphism associated with a genetic disease in a patient.

27. The method of claim 1, comprising the further step of diagnosing an infectious disease in a patient.

28. The method of claim 1, comprising the further step of devising a course of treatment for a patient suffering from an infectious disease.

29. The method of claim 1, wherein the microscopic sized target is about 0.25 $cm^2$ to about 0.5 $cm^2$ in size.

* * * * *